(12) United States Patent
Kazmierski et al.

(10) Patent No.: US 6,465,511 B1
(45) Date of Patent: Oct. 15, 2002

(54) TREATMENT OF SEPTIC SHOCK

(75) Inventors: Wieslaw Mieczyslaw Kazmierski, Raleigh; Luis Molina, Chapel Hill, both of NC (US)

(73) Assignee: Molichem Medicines, Inc., Chapel Hill, NC (US)

( * ) Notice: Subject to any disclaimer, the term of this patent is extended or adjusted under 35 U.S.C. 154(b) by 0 days.

(21) Appl. No.: 08/921,997

(22) Filed: Aug. 27, 1997

Related U.S. Application Data

(62) Division of application No. 08/537,926, filed as application No. PCT/GB94/00967 on May 5, 1994.

(30) Foreign Application Priority Data

May 6, 1993 (GB) ............................................... 9309387

(51) Int. Cl.[7] ...................... A61K 31/295; A61K 31/19; A61K 33/26
(52) U.S. Cl. ...................... 514/502; 514/574; 424/647; 424/648
(58) Field of Search ................................ 514/502, 921, 514/574; 424/647, 648

(56) References Cited

U.S. PATENT DOCUMENTS 2,891,854 A * 6/1959 Kroll et al.
5,296,466 A * 3/1994 Kilbourn et al. ............... 514/6

OTHER PUBLICATIONS

Medline Abstract, AN 81004795, 1981, Kahn et al.*
WPIDS Abstract, AN: 92–010845 [02], Aitken, R.J. et al., Abstract of GB 2245589 A., 1992.*
HCAPLUS Abstract, AN: 1984: 123531, Jeffrey, G.C. et al., Abstract of EP 97303 A1, 1984.*
Littlejohn, D. et al., J. Phys. Chem., vol. 86, No. 4, pp. 537–540, 1982.*

* cited by examiner

Primary Examiner—Russell Travers
Assistant Examiner—Shengjun Wang
(74) Attorney, Agent, or Firm—Myers Bigel Sibley & Sajovec

(57) ABSTRACT

The use of transition metal complexes in the treatment of septic shock, in particular the hypotension associated therewith and pharmaceutical formulation comprising such complexes are disclosed. The use of such transition metal complexes in the treatment of other conditions caused by pathological NO production are also disclosed.

4 Claims, No Drawings

TREATMENT OF SEPTIC SHOCK

This application is a Divisional of U.S. patent application Ser. No. 08/537,926, filed Dec. 18, 1995, which is 371 of PCT GB94/00967 filed May 5, 1998, which claims foreign priority of United Kingdom application 9309387, filed May 6, 1993.

The present invention relates to the use of transition metal complexes for the treatment of septic shock, and in particular the hypotension associated therewith.

Garavilla et al. (Drug. Dev. Res. 25:139–148, (1992)) disclose deferoxamine-manganese complexes which are superoxide dismutase mimics and improve survival following haemorrhagic and endotoxic shock. Sanan et al. (Pharmacos 28:103–105, (1985)) disclose the use of desferrioxamine mesylate to increase the survival rate of anaesthetised dogs subjected to haemorrhagic shock. U.S. Pat. No. 5,296,466 discloses the use of an iron hemoprotien for the treatment of systemic hypotension or other pathogenic syndromes induced by inappropriate NO production.

It has now been found that transition metal complexes increase the survival rate in mice subjected to endotoxin induced septic shock. The term 'transition metal complex' will be understood by one skilled in the art as a transition metal which is linked to one or more chelating agents (ligands). All transition metal complexes other than deferoxamine-maganese, hemin, diehtyldithiocarbamic acid complexes and iron hemoproteins are included.

Accordingly the present invention provides the use of a transition metal complex as hereinbefore defined in the manufacture of a medicament for the treatment of septic shock and in particular the hypotension associated therewith. Alternatively, there is provided a method of treating septic shock and in particular the hypotension associated therewith comprising administering to a mammal in need thereof an effective amount of a transition metal complex as hereinbefore defined.

Suitable transition metals include iron, copper, silver, zinc, manganese and nickel. Iron is a particularly preferred transition metal.

Suitable chelating agents include those that are coordinated to the transition metal through one or more nitrogen atoms which may be contained in a polycyclic ring system or as a substituent in an alkylene chain: through an $O^-$ or $S^-$ anion; or by virtue of a pair of electrons.

Preferred ligands include:

(i) those of formula (I)

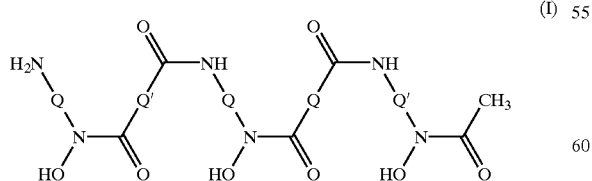

wherein Q and Q' may be the same or different and are independently a $C_{2-10}$ alkylene chain. Most preferably Q is a $C_5$-alkylene chain and Q' is a $C_2$-alkylene chain.

(ii) those of formula (II)

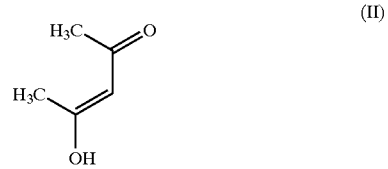

(iii) those of formula (III)

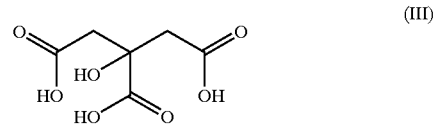

(iv) those of formula (IV)

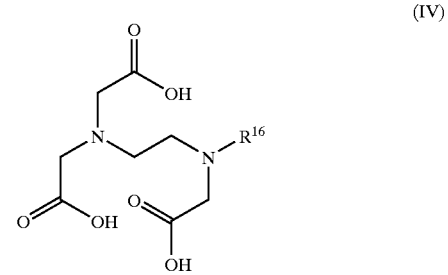

wherein $R^{16}$ is $C_{1-6}$ alkyl chain optionally substituted by a group $CO_2H$ or a group $NR^{17}R^{18}$ wherein $R^{17}$ and $R^{18}$ are independently selected from hydrogen or $C_{1-4}$ alkyl optionally substituted by a group $CO_2H$.

(v) those of formula (V)

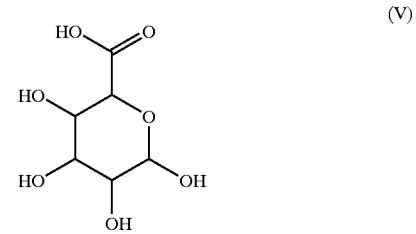

(vi) those of formula (VI)

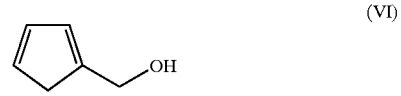

(vii) those of formula (VII)

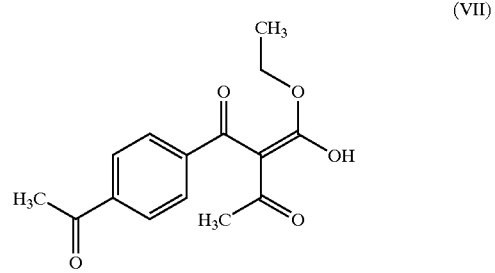

(viii) those of formula (VIII)

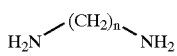

wherein n is 1 to 6, preferably 2.

(ix) those of formula (IX)

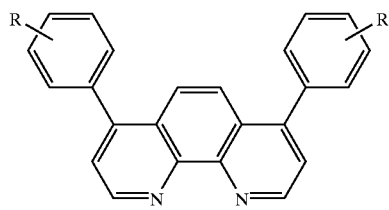

wherein R is a $C_{1-6}$ sulphonic acid or carboxylic acid group.

(x) those of formula (X)

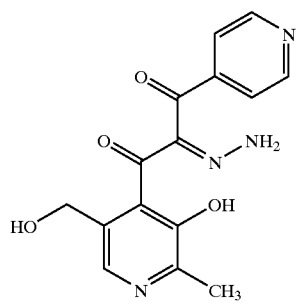

(xi) those of formula

The ligands hereinbefore described are shown in their neutral form, although they can also exist in ionic form, e.g. as a cation or anion. The exact stoichiometry of metal to ligand depends on their electronic properties, e.g. charge and the number of coordination centres. The invention is intended to include all possible stoichriometric alternatives.

Specifically preferred complexes include:
Ferrioxamine B
Ferric Pyridoxal Isonicotinoyl Hydrazone
Tris (acetylacetonato)manganese (III)
iron (III) citrate
Diethylenetriaminepentaacetic acid Iron (III)
Ethylenediaminetetraacetic acid Iron (III)
Ferrous gluconate
1,1'-ferrocenedimethanol
Ethyl α-acetyl-4-(methoxycarbonyl)benzoylacetate, Copper (II)
Tris (ethylenediamine) nickel (II) sulfate
Hexaaminenickel (II) Chloride
Bathopheneanthroline disulphonic acid Most preferred complexes are ferrioxamine B and diethylenetriaminepentaacetic acid Iron (III).

It is believed that the transition metal complexes of the present invention may act by scavenging nitric oxide (NO) in the body. Therefore, in addition to being of use in the treatment of septic shock the transition metal complexes may also be of use in the treatment of other conditions caused by pathological NO production. Accordingly the present invention further provides the use of a transition metal complex in the manufacture of a medicament for the treatment of conditions caused by pathological NO production.

A transition metal complex of the present invention may be of use during therapy with cytokines such as TNF, IL-1 and IL-2 or therapy with cytokine-inducing agents, for example 5,6-dimethyl xanthenone acetic acid; as an adjuvant to short term immunosuppression in transplant therapy; in patients suffering from inflammatory conditions in which an excess of NO contributes to the pathophysiology of the condition, for example adult respiratory distress syndrome and myocarditis; and in autoimmune and/or inflammatory conditions, such as arthritis and rheumatoid arthritis. Other conditions in which such transition metal complexes may be of use include cerebral ischemia, CNS trauma, epilepsy, AIDS dementia, chronic pain, schizophrenia and conditions in which non-adrenegic, non-cholinergic nerve may be implicated such as priapism, obesity and hyperphagia.

The transition metal complexes of the present invention may be administered alone or in conjunction with another therapeutic agent, for example a NO synthase inhibitor such as an arginine derivative e.g., L-NMMA. Accordingly, a yet further aspect of the invention provides the use of a transition metal complex in conjunction with a NO synthase inhibitor in the manufacture of a medicament for the treatment of conditions caused by pathological NO production.

A further aspect of the present invention provides a transition metal complex as hereinbefore defined other than ferrioxamine B for use in medicine.

Whilst it may be possible for the transition metal complexes to be administered as the raw chemical, it is preferable to present them as a pharmaceutical formulation. According to a further aspect, the present invention provides a pharmaceutical formulation comprising a transition metal complex as hereinbefore defined other than ferrioxamine B together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. Most suitably, the formulation is suitable for oral or parenteral administration. The formulations may conveniently be presented in unit dosage form and may be prepared by any of the methods well known in the art of pharmacy. All methods include the step of bringing into association the transition metal complex ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The transition metal complexes of the invention may be administered orally or via injection at a dose of from 0.1 to 100 mg/kg per day, preferably 1 to 50 mg/kg per day. When the transition metal complexes are given by injection, this will normally be in the form of an intravenous bolus or by infuision, preferably the latter. The dose range for adult humans is generally from 70 mg to 2.5 g/day and preferably 150 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The dose of the transition metal complexes vary according to the potency and the dose at which adverse pharmacological effects become evident. The man skilled in the art will take these factors into account when determining the dose of compound to be administered.

The activity of representative compounds of the present invention will now be described by way of example only:

EXAMPLE 1

Materials

Ferrioxamine B (deferoxamine-Fe(III)) was synthesized by complexation reaction of Fe(III) salt (specifically $FeNH_4(SO_4)_2 \cdot 12H_2O$) with deferoxamine mesylate. Deferoxamine mesylate is N-[5-[3-[(5-amino-pentyl)hydroxycarbamoyl]propionoamido]pentyl]-3-[[5-(N-hydroxyactemido)-pentyl]carbamoyl]propionohydroxamic acid monomethanesulfonate(salt). The complex was then purified on a reverse phase BPLC. It was further characterized as a homogenous (single peak on HPLC) compound by $^1H$ and $^{13}C$ NMR, mass spectroscopy and elemental analysis. Deferoxamine mesylate was from Ciba-Geigy and ferric pyridoxal isonicotinoyl hydrazone and was obtained from Polysciences, Inc. (Warrington, Pa.).

Other complexes of the present invention are commercially available (e.g. from Aldrich, Milwaukee Wis., Fluka Chem. Corp., Ronkonkoma N.Y. and Pfaltz & Bauer Inc., Waterbury Conn.) or obtainable by methods known in the art.

EXAMPLE 2

Septic Shock in Vivo Mode

C. parvum/LPS-Induced Septic Shock in Mice

The Mouse Acute Septic-Shock model is used to test compounds for their capacity to ameliorate endotoxin-induced fulmimate septic shock.

Male CD-1 mice. 25–30 g (Charles River) were injected i.v. with 100 µg killed C. parvum (Coparvax Burroughs Wellcome. RTP, N.C.). Seven to ten days later the mice were injected i.v. with 20 µg E. coli 024. B6 lipopolysaccharide in the presence of the analgesic butorphenol tartrate (150 µg per mouse). The drugs were dissolved or suspended in saline for intravenous or oral dosaging 2 hrs before and at the time of endotoxin injection. Mice were monitored over the next 7 hours and at 24–48 hours for survival. The results of the compounds tested are given in Table 1.

TABLE 1

| Compound | Route | Dose mg/kg | Survivors/Total at 48 hrs | % Survival at 48 hrs |
|---|---|---|---|---|
| Contrc. | IV | | 0/8 | 0 |
| | IP | | 0/8 | 0 |
| Ferrioxamine B | IV | 5 | 7/8 | 87.5 |
| Ferric pyridoxal isonicomnoyl hydrazone | IP | 10 | 6/8 | 75 |
| Tris(acetylacetonate) manganese|II) | IP | 1 | 5/8 | 62.5 |
| | IP | 10 | 3/8 | 37.5 |
| Iron(III)citrate | IV | 1 | 5/8 | 62.5 |
| | IV | 10 | 4/8 | 50 |
| Diethylenetriaminepentaacetic acid iron(III) | IV | 1 | 8/8 | 100 |
| | IV | 10 | 4/8 | 50 |
| Ethylenediaminetetraacetic acid iron(III) | IV | 1 | 0/8 | 0 |
| | IV | 10 | 4/8 | 50 |
| Ferrous gluconate | IV | 1 | 3/8 | 37.5 |
| | IV | 10 | 6/8 | 75 |
| 1,1'-ferrocenedimethanol | IP | 1 | 5/8 | 62.5 |
| | IP | 10 | 6/8 | 75 |
| Ethyl α-acetyl-4-(methoxycarbonyl)benzoylacetate. | IP | 1 | 5/8 | 62.5 |
| | IP | 1 | 5/8 | 62.5 |
| copper(II) | IP | 10 | 3/8 | 37.5 |
| Tris(ethylenediamine)nickel(II) | IV | 10 | 5/8 | 62.5 |

TABLE 1-continued

| Compound | Route | Dose mg/kg | Survivors/Total at 48 hrs | % Survival at 48 hrs |
| --- | --- | --- | --- | --- |
| sulphate | IV | 10 | 6/8 | 75 |
| Hexaaminenickel(II)chloride | IP | 1 | 4/8 | 50 |
|  | IP | 10 | 4/8 | 50 |
| Bathopheneanthroline disulphonic acid | IV | 1 | 7/8 | 87.5 |
|  | IV | 10 | 2/8 | 25 |

IV - intravenously.
IP - intraperitoneally

What is claimed is:

1. A method of treating septic shock comprising administering to a mammal in need thereof an effective amount of a transition metal complex, wherein said transitional metal complex comprises iron linked to a ligand selected from the group consisting of a compound of Formula IV:

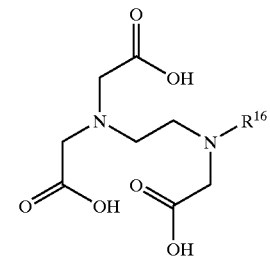

(IV)

wherein $R^{16}$ is a $C_{1-6}$ alkyl chain optionally substituted by a —COOH group or a group —$NR^{17}R^{18}$ wherein $R^{17}$ and $R^{18}$ are each hydrogen or a $C_{1-4}$ alkyl optionally substituted with a —COOH group.

2. A method according to claim 1, wherein said transitional metal complex is diethylenetriaminepentaacetic acid iron (III).

3. A method according to claim 1, further comprising administering a NO synthase inhibitor.

4. A method according to claim 3, wherein said NO synthase inhibitor is L-NMMA.

* * * * *